(12) United States Patent
Chan et al.

(10) Patent No.: US 7,931,918 B2
(45) Date of Patent: Apr. 26, 2011

(54) COLLAGEN-BASED MICROSPHERES AND METHODS OF PREPARATION AND USES THEREOF

(75) Inventors: Barbara Pui Chan, Ap Lei Chau (HK); Ming Cheuk Chan, Ap Lei Chau (HK); Kwok Fai So, Pokfulam (HK)

(73) Assignee: The University of Hong Kong, Hong Kong (HK)

( * ) Notice: Subject to any disclaimer, the term of this patent is extended or adjusted under 35 U.S.C. 154(b) by 54 days.

(21) Appl. No.: 12/166,670

(22) Filed: Jul. 2, 2008

(65) Prior Publication Data
US 2008/0317866 A1 Dec. 25, 2008

Related U.S. Application Data

(63) Continuation-in-part of application No. 11/225,108, filed on Sep. 14, 2005, now Pat. No. 7,393,437.

(60) Provisional application No. 60/609,600, filed on Sep. 14, 2004, provisional application No. 60/948,336, filed on Jul. 6, 2007.

(51) Int. Cl.
*A61K 9/16* (2006.01)
(52) U.S. Cl. .................................... 424/499; 424/489
(58) Field of Classification Search .................. 424/499, 424/489
See application file for complete search history.

(56) References Cited

U.S. PATENT DOCUMENTS

| | | | |
|---|---|---|---|
| 6,630,156 | B1 | 10/2003 | Seo et al. |
| 2006/0099268 | A1 | 5/2006 | Chan et al. |
| 2006/1022268 | | 10/2006 | Yang et al. |

OTHER PUBLICATIONS

Chan & So, "Photochemical crosslinking improves the physicochemical properties of collagen scaffolds", *J. Biomed. Mater. Res. A*, 75(3):689-701 (2005).
Chan, et al, "Photochemical cross-linking for collagen-based scaffolds: a study on optical properties, mechanical properties, stability, and hematocompatibility", *Tissue Eng.*, 13(1): 73-85 (2007).
Freiberg & Zhu, "Polymer microspheres for controlled drug release", *Int. J. Pharm.*, 282(1-2):1-18 (2004).
Fu, et al., "A potential approach for decreasing the burst effect of protein from PLGA microspheres", *J. Pharm. Sci.*, 92(8):1582-91 (2003).
Fujioka, et al., "Protein release from collagen matrices", *Adv. Drug Deliv. Rev.*, 31(3):247-266 (1998).
Hadlock, et al., "Biologic activity of nerve growth factor slowly released from microspheres", *J. Reconstr. Microsurg.*, 19(3):179-84; discussion 185-6 (2003).
Jiang, et al., "Biodegradable poly(lactic-co-glycolic acid) microparticles for injectable delivery of vaccine antigens", *Adv. Drug Deliv. Rev.*, 57(3):391-410 (2005).
Jones, et al., "Neurotrophic factors, cellular bridges and gene therapy for spinal cord injury", *J. Physiol.*, 533(Pt 1):83-9 (2001).
Lansche, "Vital Staining in Normal Eyes and in*Keratoconjunctivitis sicca*", Am. J. Ophthalmol. 60(3):520-5 (1965).
Lee, et al., "Biomedical applications of collagen", *Int. J. Pharm.*, 221(1-2):1-22 (2001).
Milev, et al., "The core protein of the chondroitin sulfate proteoglycan phosphacan is a high-affinity ligand of fibroblast growth factor-2 and potentiates its mitogenic activity", *J. Biol. Chem.*, 273(34):21439-42 (1998).
Pean, et al., "NGF release from poly(D,L-lactide-co-glycolide) microspheres. Effect of some formulation parameters on encapsulated NGF stability", *J. Control. Release*, 56(1-3):175-87 (1998).
Simmons, et al., "Evaluation of collagen cross-linking techniques for the stabilization of tissue matrices", *Biotechnol. Appl. Biochem.*, 17(Pt 1):23-9 (1993).
Sinha & Trehan, "Biodegradable microspheres for protein delivery", *J. Control. Release*, 90(3):261-80 (2003).
Yeo & Park, "Control of encapsulation efficiency and initial burst in polymeric microparticle systems", *Arch. Pharm. Res.*, 27(1):1-12 (2004).

*Primary Examiner* — Chih-Min Kam
(74) *Attorney, Agent, or Firm* — Pabst Patent Group LLP

(57) ABSTRACT

A method of manufacture of ECM microparticles incorporating bioactive molecules for drug delivery has been developed, using a modified emulsification method or a water-in-oil-phase-separation method. The microspheres are photochemically crosslinked to control the release of the bioactive molecules for better drug delivery usage without compromising the biocompatibility of the crosslinked structures. The method uses mild fabrication conditions and simple processes, no toxic chemical crosslinking reagent, which may cause cytotoxicity and calcification after implantation, no organic solvents, which may reduce drug availability and bioactivity, and no vigorous stirring action, which may fragmentize material with poor shape and mechanical stability and thus destabilize the emulsion. The resulting microparticles or microspheres are of controlled size, controlled release, highly biocompatible, and useful for drug delivery as well as cell culture.

23 Claims, 6 Drawing Sheets

US 7,931,918 B2

COLLAGEN-BASED MICROSPHERES AND METHODS OF PREPARATION AND USES THEREOF

CROSS-REFERENCE TO RELATED APPLICATIONS

This application claims benefit of and priority to U.S. Ser. No. 60/948,336 filed on Jul. 6, 2007 and is a continuation-in-part of U.S. Ser. No. 11/225,108 filed on Sep. 14, 2005, now U.S. Pat. No. 7,393,437, which claims benefit of and priority to U.S. Ser. No. 60/609,600 filed on Sep. 14, 2004. The disclosures in the applications listed above are herein incorporated by reference.

FIELD OF THE INVENTION

The present application is generally related to microparticles formed of extracellular matrix materials that provide controlled release and desirable mechanical properties, and methods of manufacture and use thereof.

BACKGROUND OF THE INVENTION

Microsphere-based drug delivery systems are advantageous because of their injectability and versatility in controlling the release patterns of the loaded drugs (Sinha and Trehan, *J. Control. Release*, 90(3):261-80 (2003)). This reduces invasiveness of multiple injections. Biocompatibility and biodegradability are necessary criteria for selecting the drug carriers. Both synthetic polymers such as polylactic acids and polyglycolic acids and natural polymers such as chitosan and alginates can be used for making microspheres for drug delivery (Sinha and Trehan, *J. Control. Release*, 90(3):261-80 (2003)). Poly-lactic-glycolic acid (PLGA) microspheres dominate this field (Pean, et al., *J. Control. Release*, 56(1-3): 175-87 (1998); Sinha and Trehan, *J. Control. Release*, 90(3): 261-80 (2003); Jiang, et al., *Adv. Drug Deliv. Rev.*, 57(3):391-410 (2005)) because it has been used for years as a suture material. However, as a polyester, PLGA has inevitable intrinsic shortcomings (Sinha and Trehan, *J. Control. Release*, 90(3):261-80 (2003)) such as low protein polymer compatibility due to the limited solubility and stability of protein in the hydrophobic PLGA matrix, and the extreme acidity of the degradation products at local injury site, which can damage cells and denature proteins. Typically fabricated by a double-emulsion technique, PLGA microspheres often show low encapsulation efficiency and poor retention of bioactivity of the encapsulated protein. Previous reports have demonstrated large burst effect of nerve growth factor ("NGF") release and loss of bioactivity as early as 48 hours (Pean, et al., *J. Control. Release*, 56(1-3):175-87 (1998); Hadlock, et al., *J. Reconstr. Microsurg.*, 19(3):179-84; discussion 185-6 (2003)). Apart from instability of the protein drugs, high initial burst and incomplete release also affect the efficiency of microsphere-based drug delivery systems (Yeo and Park, *Arch. Pharm. Res.*, 27(1):1-12 (2004)).

Strategies aiming to improve the initial rapid loss using methods enhancing the protein distribution throughout the polymer matrix (Fu, et al., *J. Pharm. Sci.*, 92(8):1582-91 (2003)) have been reported. Polymerization, emulsification, spray drying and solvent extraction or combinations of these processes are commonly used methods for preparation of polymeric microspheres (Freiberg and Zhu, *Int. J. Pharm.*, 282(1-2):1-18 (2004)). U.S. Pat. No. 6,630,156 to Seo, et al. discloses a method for producing polymer microspheres incorporating physiologically active molecules by emulsification followed by solvent extraction. These methods involve the usage of organic solvents, emulsifying stabilizer and vigorous stirring. These present chemical and mechanical stresses, which can exert damaging effects on the conformational and biological integrity of many drugs in particular proteins (Yeo and Park, *Arch. Pharm. Res.*, 27(1):1-12 (2004)). Moreover, the acidic and hydrophobic microenvironment within the degrading polymers can further damage the loaded drugs (Freiberg and Zhu, *Ins. J. Pharm.*, 282(1-2): 1-18 (2004)).

Natural extracellular matrix such as collagen has excellent biocompatibility and negligible immunogenicity (Sano, et al., *Adv. Drug Deliv. Rev.*, 31(3):247-266 (1998); Lee, et al. 2001), and excellent protein compatibility. Therefore, they are excellent candidates for protein delivery devices. These materials provide the natural extracellular milieu that stabilize proteins and potentiate or augment the activity of protein drugs such as growth factors (Lee, et al., *Int. J. Pharm.*, 221(1-2):1-22 (2001); Jones, et al., *J. Physiol.*, 533(1):83-9 (2001); Milev, et al., *J. Biol. Chem.*, 273(34):21439-42 (1998)). Moreover, degradation of these materials results in naturally occurring monomers at neutral pH that do not generate local injury or inflammation. Furthermore, these materials facilitate cell adhesion, attachment and growth that may help in efficiently delivering the signals regulating cell activities. However, their development as drug delivery devices have been overshadowed by advances in synthetic polymers due to the poor dimensional and mechanical stability, and rapid swelling properties of these natural extracellular matrix biomaterials (Yannas, et al. IV. Natural materials. In: Ratner B D, Hoffman A S, Schoen F J, Lemons J E, editors. Biomaterials Sciences—An introduction to materials in medicine. California; Academic Press, 1996: 84-93). This is because most microsphere fabrication method requires vigorous mixing that may fragment these materials (Freiberg and Zhu, *Int. J. Pharm.*, 282(1-2):1-18 (2004)). Therefore, it is almost impossible to fabricate microspheres using these materials unless chemical crosslinking has been used. However, toxicity associated with the residue chemical crosslinking agent prevents its use in drug delivery (Sinha and Trehan, *J. Control. Release*, 90(3):261-80 (2003)). US Patent Application 20060222680 by Yang and Mark discloses a method of preparing chemically crosslinked collagen microspheres. Chemical crosslinking using glutaraldehyde is efficient in crosslinking the polymers with enhanced mechanical and shape stability. However, it compromises the biocompatibility of the crosslinked structures because the toxic residual chemicals and degradation products induce cytotoxicity and calcification (Simmons, et al., *Biotechnol. Appl. Biochem.*, 17 (Pt 1):23-9 (1993)).

Drug release from a matrix carrier is controlled by either diffusion or degradation or in many cases combinations of two. Many formulation parameters, including the drug, matrix and environmental factors affect the initial burst and the rate of release (Yeo and Park, *Arch. Pharm. Res.*, 27(1): 1-12 (2004)). Drug factors such as surface charge, hydrophobicity, loading and solubility in the continuous phase of the drug may affect the interaction between the drug and the matrix and thus the initial burst and release rate. Matrix factors such as the hydrophilicity, concentration, porosity, density, mesh size and swelling properties of the matrix also affect the interaction between the drug and the matrix and thus the initial burst and release rate.

It is therefore an object of the present invention to provide microparticles formed of ECM materials that provide controlled release of bioactive materials and desirable mechanical properties, and methods of manufacture and use thereof.

It is another object of the invention to provide microparticles formed of ECM materials that are highly compatible with bioactive materials and particularly peptides, polypeptides and proteins.

It is a further object of the present invention to provide methods of manufacture that are simple, mild, and non-toxic, without vigorous stirring or organic solvents.

SUMMARY OF THE INVENTION

A method of manufacture of ECM microparticles incorporating bioactive molecules for drug delivery and/or for tissue engineering has been developed, using a modified emulsification method or a water-in-oil-phase-separation method. The microspheres are photochemically crosslinked to control the release of the bioactive molecules for better drug delivery usage and to form structure without compromising the biocompatibility of the crosslinked structures. The method uses mild fabrication conditions and simple processes, no toxic chemical crosslinking reagents, which may cause cytotoxicity and calcification after implantation, no organic solvents, which may reduce drug availability and bioactivity, and no vigorous stirring action, which may fragmentize material with poor shape and mechanical stability and thus destabilize the emulsion. The resulting microparticles or microspheres are of controlled size, controlled release, highly biocompatible, and useful for drug delivery as well as cell culture.

DETAILED DESCRIPTION OF THE INVENTION

I. Definitions

Extracellular matrix ("ECM") as used herein refers to any material produced by cells and secreted into the surrounding medium, but is usually applied to the non-cellular portion of animal tissues. The ECM of connective tissue is particularly extensive and the properties of the ECM determine the properties of the tissue. In broad terms there are three major components: fibrous elements particularly collagen, elastin, or reticulin), link proteins (eg. fibronectin, laminin), and space-filling molecules (usually glycosaminoglycans).

"Microparticles" as used herein includes microspheres (generally spherical in shape) and microcapsules (generally spherical in shape with a hollow centre), as well as particles of irregular shape, and are typically in the range of between 0.5 to less than 1000 microns in diameter.

II. Methods of Manufacture

Figure 1:
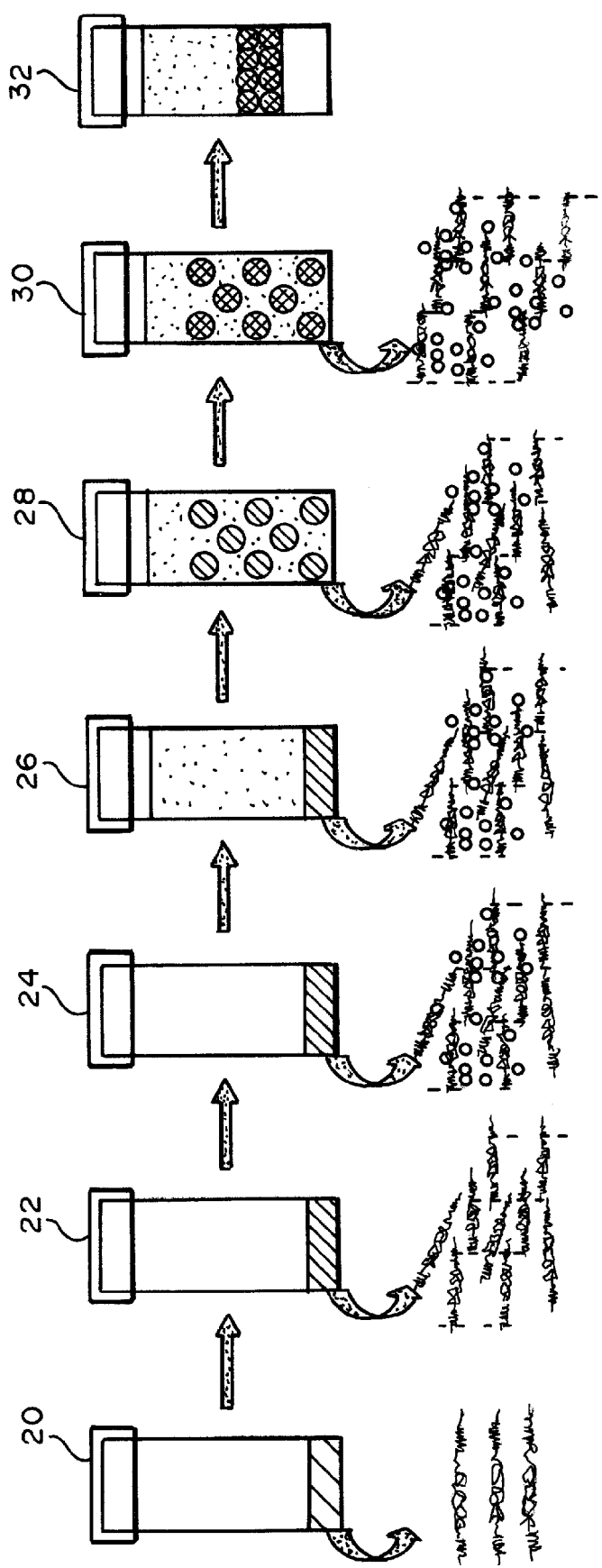
FIG. 1 is a flow chart showing the process of preparing the microspheres using the methods disclosed herein. A solution containing collagen monomers (20) is induced to initiate the sol-gel transition of collagen. The sol-gel transition is decelerated after a period of time to form a solution containing collagen monomers and slowly forming collagen polymers (22). One or more bioactive molecules are then added to the solution (24). An oil phase is then added to the aqueous solution containing the collagen monomers, slowly forming collagen polymers and one or more bioactive agents (26). Emulsions of the aqueous and oil phases are then formed to produce aqueous droplets containing the collagen monomers, slowly forming collagen polymers and one or more bioactive agents suspended in a continuous oil phase (28). The emulsions are then subjected to conditions that cause the acceleration or resumption of the sol-gel transition causing the aqueous microdroplets to solidify and encapsulate the bioactive molecules within the homogenous solid mass of the microspheres (30). The solid microspheres are the separated from the liquid phase which contains both the aqueous and oil phases using standard techniques (32).
Figure 2:
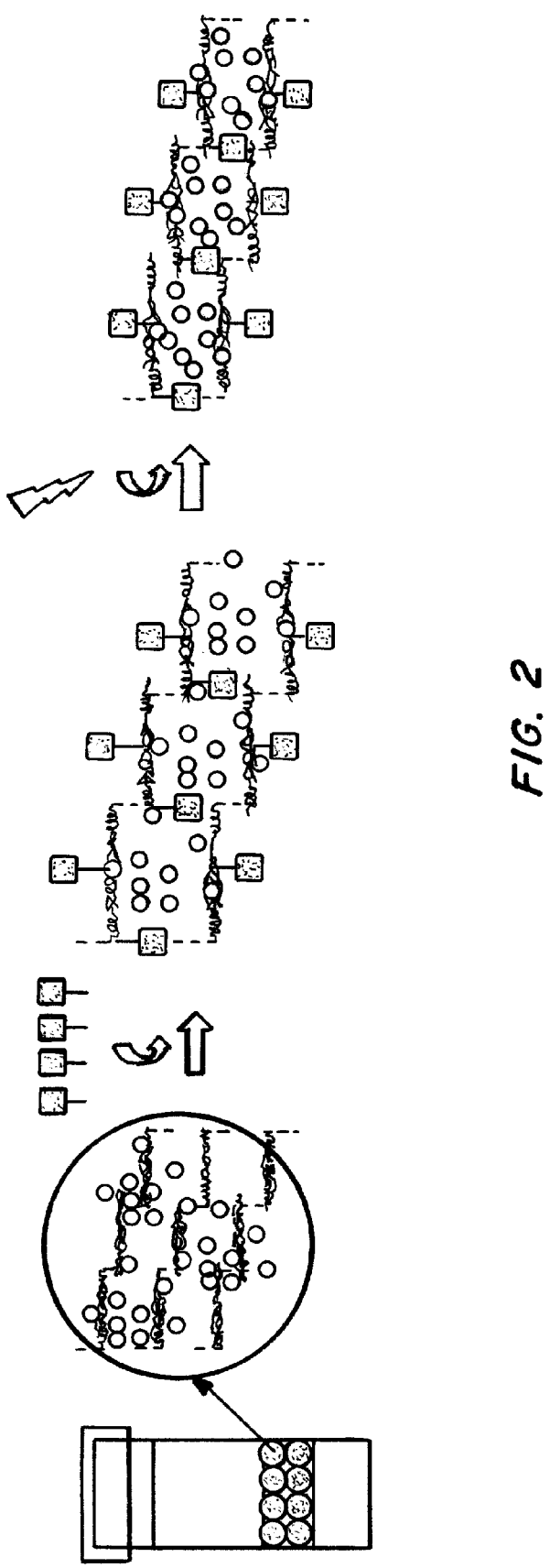
FIG. 2 is a flow chart showing the process of photochemical crosslinking of the microspheres. Solidified collagen microspheres are immersed in a solution of photosensitizer for a period of time to allow the photosensitizer to bind to the collagen. The microspheres in water or an isotonic solution are then exposed to a light source of an appropriate level of energy for a period of time, resulting in a crosslinked collagen network.
Figure 3:
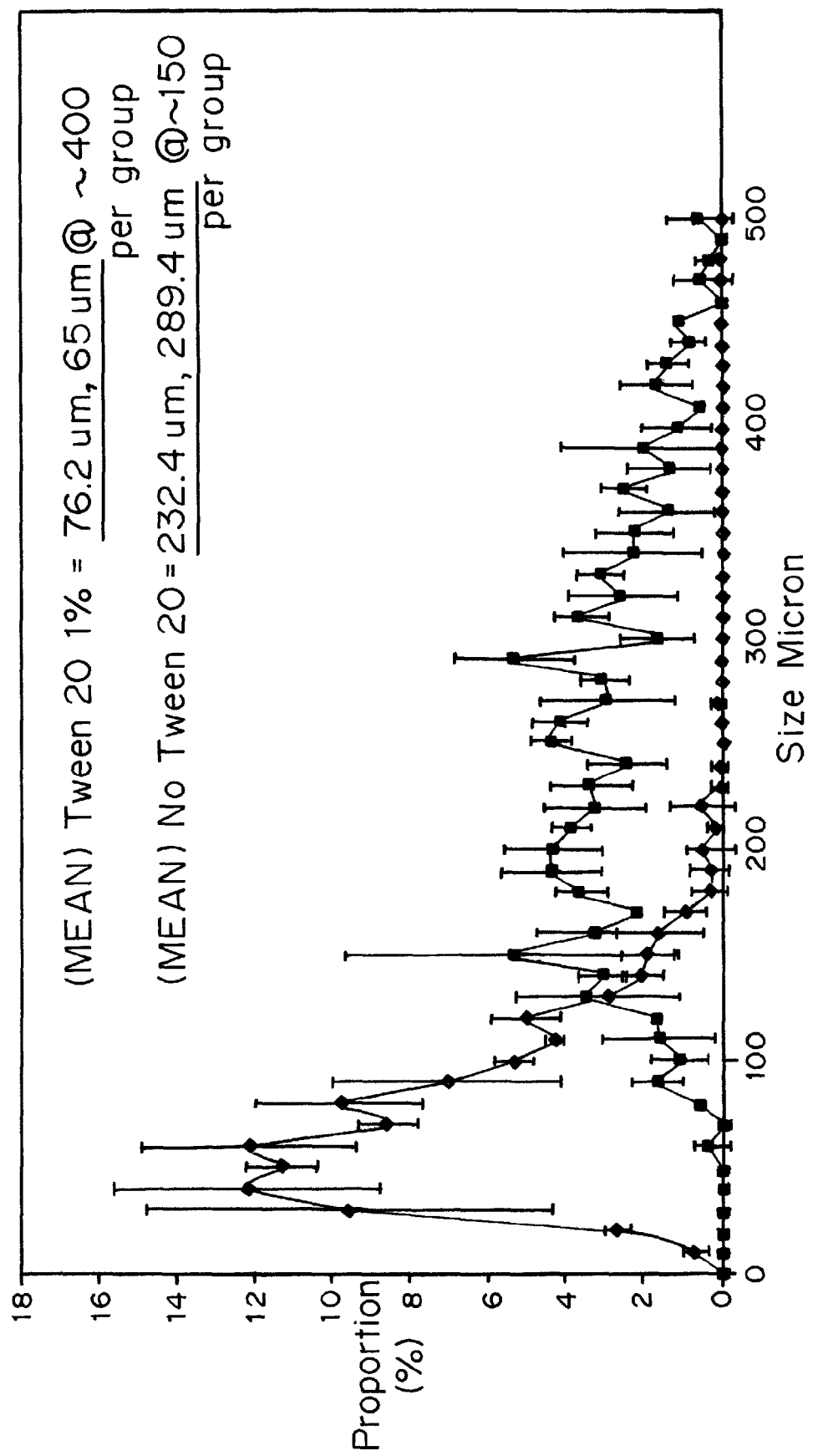
FIG. 3 is a line graph showing the size distribution of microspheres, with 1% TWEEN®20 (-♦-) or without TWEEN®20 (-■-). Size distribution is graphed as proportion of microspheres (percent) as a function of size (microns).

The method of preparing microspheres of collagen and composites of collagen and other extracellular matrix components, as depicted in FIG. 1, comprises the steps of:

(1) providing a solution of collagen monomers or mixture of collagen monomers and other natural extracellular matrix components;

(2) initializing the sol-gel transition of collagen or precipitation of collagen and other matrix components;

(3) decelerating the sol-gel transition or the precipitation process for appropriate period of time;

(4) incorporating one or more bioactive molecules into the aqueous gelling mixture at appropriate time;

(5) mixing the aqueous phase with an oil phase with appropriate viscosity for appropriate time at appropriate agitation rate with or without the presence of surfactant;

(6) accelerating the sol-gel transition or the precipitation process after appropriate period of time;

(7) separating the solid microspheres from the liquid phase which consists of both the oil phase and the aqueous phase by methods such as centrifuging the mixture at appropriate speed.

Although described with reference to microparticles, additional structures can be formed, and/or the microparticles can be formed into additional structures as coatings, encapsulated or incorporated into other materials that act as binders, for example, for use as tissue engineering matrices.

A. Materials
1. ECM Materials

Natural extracellular matrix components include, but are not limited to, collagen of different phenotypes such as type I, II and III, denatured collagen gelatin, proteoglycans, hyaluoronic acid, elastin, both extracted from naturally occurring sources such as human and animal tissues or synthesized. These can be obtained using published procedures, or purchased from any of several suppliers. Some extracellular matrix components such as collagen, gelatin and hyaluronic acid can be induced to undergo sol-gel transition under certain specific conditions while other natural extracellular matrix components such as collagen and GAGs (glycosaminoglycans) precipitate with each other at other specific conditions.

In a preferred embodiment, the extracellular matrix is collagen type I, type II, type III, or mixtures thereof. This may be of human or animal or synthetic origin. In one embodiment, collagen is from rat tail, bovine Achilles tendon, porcine skin, or human placenta and from different fractions of extracted collagen such as acid-soluble fraction, pepsin digested fraction, and insoluble fraction. In another embodiment, proteoglycan is from shark cartilage. The collagen monomers can be from fractions of collagen extracted from animal sources, such as the acid-soluble fraction, pepsin digested fraction, or insoluble fraction.

2. Bioactive Materials

Any therapeutic, prophylactic or diagnostic material can be incorporated into the microspheres. These may be proteins or peptides, saccharides or polysaccharides, lipids or conjugates or complexes thereof, nucleic acids such as DNA, RNA or complexes thereof, or other inorganic or organic molecules, for example, antibiotics, chemotherapy drugs, etc.

The microspheres are manufactured using mild fabrication conditions that are particularly suitable for encapsulating proteinaceous bioactive agents. In one embodiment, the therapeutic, prophylactic or diagnostic material that is encapsulated is a peptide, polypeptide or protein. Preferred materials include growth factors such as but not limited to cytokines and growth factors, for example, nerve growth factor (NGF), basic fibroblast growth factor (bFGF), platelet-derived growth factors (PDGF), transforming growth factors beta (TGF-β), and insulin growth factor I (IGF-I). These factors are usually water soluble and will be mixed with the gelling mixture thoroughly so that any droplets formed during emulsification will contain evenly distributed factors. Molecules stabilizing these bioactive factors such as bovine serum albumin ("BSA") or human serum albumin ("HSA") for NGF can also be included.

3. Oils, Surfactants and Other Emulsifying Agents

The oil phase typically will include vegetable oils such as olive oil or corn oil, organic oils such as paraffin oil, synthetic oils such as silicone oil or mixtures of different oils, depending on the viscosity of the gelling mixture, for example, paraffin oil at a volume ratio between 1:1 to 1:100, preferably between 1:6 and 1:10.

The solution should preferably have a viscosity in the range of between 1 and 1000 mPascal second, most preferably 20-100 mPas. The volume ratio referred to herein is the ratio of volume of the ECM component (collagen)-bioactive protein mixture to the volume of oil.

A surfactant may be added to either or both the aqueous solution or the oil. A preferred surfactant is TWEEN® 20 or 180, SDS, or TRITON® X-100, most preferably TWEEN®20, added to 0.1, 1, 10%, 20% preferably 10% of liquid mixture.

B. Reaction Conditions
1. Providing a Solution of Collagen Monomers or Mixture of Collagen Monomers and Other Natural Extracellular Matrix Components.

The ECM material is provided as an aqueous solution of monomer, preferably in a range of 0.5-30 mg/ml, more preferably 7 mg/ml. The pH of acid soluble collagen is around 3. No dispersant or buffer is typically needed. An aqueous collagen solution typically is adjusted to the acid pH with an acidic solution such as 0.02N acetic acid.

2. Initializing the Sol-Gel Transition of Collagen or Precipitation of Collagen and Other Matrix Components.

The sol-gel transition or the precipitation process is usually initiated by a chemical and/or physical reaction. In one embodiment, collagen monomers are initiated to polymerize or reconstitute to native fibrils by raising the pH such as addition of sodium hydroxide or sodium bicarbonate, the ionic strength or the temperature. In another embodiment, collagen monomers are mixed with GAGs and precipitation is initiated by mechanical actions such as stirring, vortexing, agitating and rotating. In another embodiment, sol-gel transition of composite of acid-soluble collagen type I and II is initiated by raising the pH of the mixture by an alkali such as sodium hydroxide or sodium bicarbonate or ammonium hydroxide, preferably to a pH between 4 and 14, most preferably between 8 and 14. In another embodiment, collagen monomers, or collagen monomers mixed with other ECM components, are initiated to polymerize or reconstitute to native fibrils by increasing the temperature of the solution.

3. Decelerating the Sol-Gel Transition or the Precipitation Process for Appropriate Period of Time.

These natural extracellular matrix components will solidify during polymerization, sol-gel transition and precipitation until the completion of the process or until reaching the equilibrium after certain period of time. Before these components are completely solidified, the mixture is subjected to conditions at which the polymerization or the precipitation process is decelerated or even temporarily inhibited by controlling the same or another parameter. This step is for incorporation of the bioactive molecules into the mixture and for formation of emulsions.

Methods for decelerating the process include keeping the temperature as low as possible, such as between 2-25° C., most preferably 4° C. or lower but above 0° C. Other methods include adjusting the pH to lower than 7 such as 4, or lowering the ionic strength of the solution, such as by using 0.1×PBS.

In one embodiment, the collagen gelling mixture is subjected to an environment of lower temperature such as 4° C. In another embodiment, the collagen and GAGs mixture is subjected to an environment without mechanical disturbance. In another embodiment, the sol-gel transition of the matrix components is decelerated at 0, 1, 10 or 60 seconds, 3, 5, 10 or 60 minutes, 2, 4, 8 or 24 hours, or 2, 4, 7 or 14 days, throughout other steps before resuming the sol-gel transition. In a preferred embodiment, the sol-gel transition is decelerated at 15 minutes.

4. Incorporating One or More Bioactive Molecules into the Aqueous Gelling Mixture at Appropriate Time.

Single or multiple bioactive molecules can be incorporated into the mixture, either as a liquid or as a powder. Bioactive molecules are added to a therapeutically effective concentration. In many cases, such as with most protein growth factors, these are effective at pictogram to nanogram levels. Bioactive agents may also be incorporated in the milligram level. These will typically uniformly disperse, especially if the molecules are water soluble.

5. Mixing the Aqueous Phase with an Oil Phase with Appropriate Viscosity for an Appropriate Time at an Appropriate Agitation Rate with or without the Presence of Surfactant.

Emulsions will be formed between the gelling or precipitating mixture of natural extracellular matrix components and an oil phase by methods including, but are not limited to, shaking, agitating, mixing, stirring, and vortexing, without fragmentizing the gelling mixture and disturbing the sol-gel transition process, preferably with a loading device, at appropriate volume ratios, with appropriate viscosity, at appropriate agitation speed for appropriate period of time. The viscosity will typically be between 1-1000 mPas (the unit milliPascal second), preferably 20-100 mPas, with an agitation speed between 800-10,000 rpm, preferably 2000 rpm, for a period of time between 1 second to 24 hours, preferably 10 seconds, with a volume ratio of the aqueous protein mixture to oil between 1:1 to 1:100, preferably 1:10.

In one embodiment, an ECM gelling mixture is mixed with an oil phase such as olive oil, silicon oil, corn oil, or mixtures of different oil, depending on the viscosity of the gelling mixture. The oil phase typically will include vegetable oils such as olive oil or corn oil, organic oils such as paraffin oil, synthetic oils such as silicone oil or mixtures of different oils, depending on the viscosity of the gelling mixture, for example, paraffin oil at a volume ratio between 1:1 to 1:100, preferably between 1:6 and 1:10. The preferred material is paraffin oil at a volume ratio between 1:1 to 1:100, preferably 1:10, for a period of time such as 1, 10, 20, 30, 40, 50, or 60 seconds, 1, 2, 5, 10, or 60 minutes, or 2, 4, 8, or 24 hours. The period of time is determined by the rate of sol-gel transition, total volume of the collagen protein mixture and the oil, viscosities of collagen protein mixture and the oil phase, the power and frequency of the mechanical mixing machine, the size and mass of the containers holding the mixtures, temperature, etc. The examples demonstrate the ranges based on the maximal power of a custom-made mixing machine in a 10 ml plastic container, 7 mg/ml collagen with 25 mg BSA, volume ratio of 1:6 for collagen mixture to oil ratio, at 25° C. In a preferred embodiment, the material is mixed for 10 seconds, at one fourth of the maximal agitation speed of this custom-made mixing device. If the speed is too low, it will not provide sufficient energy to emulsify the mixture. If the speed is too fast, phase inversion will occur so that oil droplets will be trapped within the droplets of collagen gelling mixture and collagen fragments will be obtained. If the time for emulsification is too short, the material will coalesce to form microspheres with large diameter size. If the time for emulsification is too long, phase inversion and fragmentation will occur.

In order to further stabilize the emulsions formed, surfactants, including but are not limited to TWEEN® 20 can be introduced during this process, at a concentration of 1, 10, 20% preferably 1%.

6. Accelerating the Sol-Gel Transition or the Precipitation Process after an Appropriate Period of Time.

Immediately after the emulsion formation, the emulsions will be subjected to an environment accelerating or resuming the sol-gel transition or the precipitation process at a maximal rate for a period of time. This is to solidify the microdroplets in the emulsions so as to encapsulate the incorporated bioactive molecules within the homogenous solid mass of the microspheres. This also prevents coalescence so as to reduce the microsphere size. The same process parameters are manipulated.

In one embodiment, collagen emulsions are subjected to an environment with raised temperature at 12° C., 25° C., 37° C., preferably 37° C., for a period of time such as 10, 30 or 60 seconds, 2, 5, 10, 30 or 60 minutes, 2, 4, 8 or 24 hours, or 2, 4 or 7 days, preferably 45 minutes, until the sol-gel transition is completed or reached equilibrium thus forming solidified microspheres, depending on the properties of the sol-gel transition of the matrix component. In another embodiment, the rate of gelation of the collagen microspheres is controlled by varying the concentration of a phosphate buffered saline ("PBS", 0.01 M phosphate buffered saline, NaCl 0.138 M; KCl 0.0027 M; pH 7.4, at 25° C.) buffer used at 1×, 5× and 10× preferably 5×. In another embodiment, the emulsions are subjected to an environment with pH raised to pH 14 by incubating the emulsions in an alkaline chamber filled with ammonia for solidification.

7. Separating the Solid Microspheres from the Liquid Phase Which Consists of Both the Oil Phase and the Aqueous Phase.

The solidified microspheres are separated using standard techniques such as filtration, sedimentation, centrifugation, etc.

This method provides a simple process without involvement of organic solvents and vigorous mechanical and chemical stresses, which are known to reduce the bioactivity of drugs particularly protein drugs. The solidified microspheres are easily separated from both liquid phases, which consist of both the aqueous and the oil phases. In one embodiment, the mixture is centrifuged at a speed such as 1, 10, 100, 1000 or 10000 rpm, preferably 4000 rpm, without fragmentizing the microspheres, for a period of time such as 1, 5, 10, 30 or 60 seconds, 2, 5, 10, 30 or 60 minutes, or 2, 4, 8 or 24 hours, preferably 10 minutes.

III. Methods of Further Modifying Microparticles

Microspheres are obtained having size distributions ranged from 0.05 to 1000 microns in diameter, preferably 50-100 microns. These microspheres have a smooth surface or a rough surface when dehydrated.

The initial burst effect can be reduced and the release pattern of the bioactive molecules from the microspheres controlled by methods including, but not limited to, photochemical crosslinking, comprising the steps of (1) equilibrating the microspheres with a photosensitizing reagent in an appropriate dose; (2) rinsing the microspheres thoroughly to remove excess photosensitizer; and (3) irradiating the microspheres with a light source of appropriate level of energy for a period of time.

A. Reagents

Photosensitizing reagents include chromophores able to be activated by photons at particular wavelengths, including, but not limited to, fluorescein, eosin, rose Bengal ("RB"), and methylene blue. Photosensitizing reagents include RB, which has a spectrum of absorption up to approximately 600 nm. In addition to the UV region, there are two absorption peaks at approximately 514 nm and 550 nm.

RB has high absorption efficiency and therefore is a very efficient photosensitizing reagent. Rose Bengal is a vital dye that has been used in clinical diagnostic for opthalmologic diseases for decades (Lansche R. K., "Vital Staining in Normal Eyes and in Keratoconjunctivitis Sicca", Am. J. Opthalmol. 60(3):520-5 (1965)). It is a safe reagent to use. Rose Bengal is a fluorescent photosensitizing reagent that is water soluble. However, aggregates may form at high concentrations such as >1% (w/v) and therefore the preferred concentration of rose Bengal is ranged from 0.00001% to 0.01%. Rose Bengal solution is prepared in darkness using a solution such as distilled water or PBS and ethanol; preferably water.

B. Method of Crosslinking

1. Soaking Microspheres in Photosensitzer

The microspheres are immersed in a solution of photosensitizer for 1, 10, 30 or 60 seconds, 2, 5, 10, 30 or 60 minutes, or 2, 4, 8 or 24 hours, preferably 10 minutes. The concentration of the photosensitizing reagent ranges from 0.00001% to 1%, preferably 0.001%. Representative photosensitizing reagents include fluorescein, Rose Bengal, methylene blue, eosin, and porphyrins.

Preferably the microspheres are into contact with the photosensitizing reagent for a period of time ranging from 5 seconds to 100 hours, preferably 10 minutes. Most preferably, excess reagent is removed from the microspheres by washing.

Photochemical crosslinking is a non-thermal, non-toxic and rapid technique to crosslink the collagen-based materials without compromising the biocompatibility. This method is disclosed in US published Patent Application No. 20060099268. Photochemically crosslinked collagen has been demonstrated to have significantly enhanced physicochemical properties (Chan and So, *J. Biomed. Mater. Res. A*, 75(3):689-701 (2005), Chan, et al., *Tissue Eng.*, (1): 73-85 (2007)). Apart from increased mechanical properties, thermal and chemical stability, the technique has been shown to dramatically reduce the pore size of collagen structures and the swelling rate, which alter the interactions between the collagen network and the loaded protein. These properties are important matrix parameters affecting the initial burst and the release rate of the drug.

2. Exposing Microspheres to Light Source

The microspheres in water or an isotonic solution are brought to a light source, such as a UV source, a laser, LED or other source of visible light. The amount and power intensity of the light affect the extent of crosslinking as it is proportional to the number of photons. Suitable light sources include an argon laser, at a wavelength of 514 nm, or multiline green laser. Other lasers which Rose Bengal absorbs can also be used. The argon laser can be continuous or pulsed. Laser will be delivered at an irradiance of 0.0001, 0.001, 0.01, 0.1, 1, or 10 W/cm$^2$, preferably 0.2 W/cm$^2$. The duration of irradiation is 1, 10, 100, 1000, or 10000 seconds, preferably 100 seconds. The total energy of light delivered to the microspheres is 0.5, 1, 5, 10, 100, or 1000 J, preferably 20 J.

The entire process can be performed under sterile conditions. During crosslinking, laser is delivered to the microspheres through a transparent container.

C. Photocrosslinked Microspheres

Photochemically crosslinked microspheres have size distributions ranging from 0.05 to 1000 microns in diameter, preferably 50-100 microns. The photochemically crosslinked microspheres have smooth surface or rough surfaces when dehydrated.

Photochemical crosslinking reduces the release rate of incorporated bioactive molecules by both diffusion and degradation. Photochemical crosslinking strengthens the collagen fibrils that results in ultra-fine microstructures with micron-sized pores interconnected with nano-sized fibrous network in freeze-dried structures. This may reduce the rate of diffusion and thus the release of the incorporated bioactive molecules from the liquid phase trapped among the fibrous network. Photochemical crosslinking also reduces the rate of disintegration of collagen structures in physiologically relevant conditions. Photochemical crosslinking also enhances retention of bioactive molecules with the matrix meshwork. This reduces the amount and rate of release of the incorporated bioactive molecules in dehydrated samples upon rehydration. The crosslinked microspheres release the incorporated bioactive molecules with a significantly reduced initial burst and first order release kinetics. Photochemical crosslinking does not alter the mesh size of the hydrated collagen fibril meshwork in the microsphere but may alter the interactions such as ionic, electrostatic and hydrophobic interactions, between the crosslinked collagen structures and the loaded proteins and thus hinder the release of proteins. The release can be sustained for a long term without compromising the bioactivity of the incorporated bioactive molecules.

Both uncrosslinked and photochemically crosslinked microspheres with incorporated bioactive molecules can be used to deliver the bioactive molecules by direct injection into the injury sites systems including but are not limited to neurological and musculoskeletal systems.

D. Storage of Microspheres

The microspheres can be further processed and stored, for example, by dehydrating the microspheres rapidly or gradually by immersing in absolute alcohol or alcohol of increasing concentrations; freeze-drying, critical point drying, oven drying, air drying, acetone-drying, or dispersing in glycerol, or other conditions without denaturing both the matrix component of the microspheres and the incorporated bioactive molecules. The alcohol dehydration method extracts water from the microspheres by immersing in absolute alcohol for several rinses or a series of increasing concentration of alcohol, ranging from 10% to 100%, preferably 50% to 100%, each for a period of time ranging from 1 minute to 10 days, preferably 30 minutes. The microspheres can be stored as slurry or dried using dehydration gradient method.

E. Applications of Microspheres

The microspheres are useful for drug delivery and for three dimensional cell culture and implantation because these microspheres, unlike the chemically crosslinked ones, do not have toxicity.

The present invention will be further understood by reference to the following non-limiting examples.

EXAMPLES

Example 1

Preparation of Collagen Microspheres Incorporated with BSA or Myoglobin

Rattail collagen type I solution at a concentration of 7 mg/ml in 0.02N acetic acid was neutralized with 1N sodium hydroxide in the presence of 10× phosphate buffered saline with a final concentration of 0.5×. The gelling mixture was placed inside an ice water bath at 4° C. to slow down the polymerization rate for 1 minute. Sample proteins such as BSA and myoglobin can be incorporated. BSA (4 mg) was added to the mixture and thoroughly mixed well.

A mixture of olive oil and silicon oil at a ratio of 1:1 was laid down on the aqueous gelling mixture at a volume ratio of 6:1. A nonionic surfactant, Tween 20, was added to the aqueous phase before emulsification. The container of the mixture was placed on a mixing device. The mixture was agitated at maximal speed (3000 rpm) for 30 seconds. The emulsions formed were then placed in a 37° C. water bath to speed up the polymerization. The mixture was incubated for 30 minutes until equilibrium. The mixture was centrifuged briefly at 4000 rpm for 10 minutes to separate the solid microspheres from the liquid phases including an aqueous and an oil phase. After discarding the oil and the liquid phase, the microspheres were rinsed twice and ready for injection or subsequent release experiments.

Example 2

Photochemical Crosslinking of Collagen Microspheres

Microspheres obtained from procedures described in Example 1 were immersed in a solution of Rose Bengal photocrosslinker, "PC") at a concentration of 0.001% (w/v) in water for 10 minutes. Excess Rose Bengal was discarded and the microspheres were rinsed. The microspheres were resuspended in water and placed in a 4-well plate culture dish. An Argon laser at 514 nm was used to irradiate the microspheres at 0.02 W/cm$^2$ for 100 seconds. Immediately after the irradiation, the microspheres were rinsed in water. The microspheres were then ready for injection or subsequent experiments.

Example 3

Dehydration of Collagen Microspheres

Microspheres were immersed in 100% alcohol for 30 minutes and the extraction of water from the microspheres was repeated for three times. A gradual increase in alcohol concentration was used to improve the microsphere surface smoothness. The collagen microspheres were immersed in 50% v/v alcohol for 20 minutes, 70% alcohol for 30 minutes twice, 80% alcohol twice, 90% alcohol twice and 100% alcohol twice.

Example 4

Morphological Analysis of Microspheres

Microspheres were fixed in 0.25% glutaraldehyde for 4 hours at room temperature and then dried by critical point drying. The microspheres were then thoroughly rinsed in large volume of water. The microspheres were dehydrated by critical point drying and mounted on the sample stage with carbon cement. The samples were sputtered with gold and analyzed using scanning electron microscopy (SEM). The results show that the microspheres are much stronger and have smaller porosity when crosslinked.

Example 5

Characterization of Microstructure of Photochemically Crosslinked Collagen

Reconstituted collagen gel was photochemically crosslinked by varying the photosensitizing reagent and light dosage. Glutaraldyhyde was used as a positive control for chemical crosslinking. The treated structures were freeze-dried. Cross-sections of the collagen scaffolds were sputtered with gold for SEM analysis of the porous structures. This showed that both glutaraldehyde and photochemically crosslinked collagen scaffolds have fine microstructures with interconnected fibers with nanosized fibers and micro-sized pores. In the control groups, only macrostructures with membrane like structures were found.

Tables 1-3 show the change in microstructures of collagen after photochemical crosslinking and the dose-dependence on photosensitizing reagent concentration and fluence. Table 4 shows the change in fiber size and mesh size after photochemical crosslinking and surfactant treatment.

TABLE 1

Pore size distributions of collagen scaffolds.

| Treatment groups | Pore size (microns)/ Mean ± SD | |
|---|---|---|
| | Long axis | Short axis |
| Control | 366 ± 61 | 224 ± 44 |
| Laser only | 398 ± 18 | 279 ± 11 |
| Dye only | 267 ± 12 | 170 ± 10 |
| Photochemical crosslinking (20J, 0.01% dye) | 1.9 ± 0.1 | 1.2 ± 0.1 |
| Glutaraldehyde (0.25%, 2 hrs) | 1.8 ± 0.0 | 1.3 ± 0.0 |

TABLE 2

Pore size distributions of collagen scaffolds with different laser energy dosage and post-irradiation incubation time.

| Duration of incubation | 0 hr | | 3 hrs | | 24 hrs | |
|---|---|---|---|---|---|---|
| Laser energy (J) | Long axis | Short axis | Long axis | Short axis | Long axis | Short axis |
| 0 | No microstructure | | No microstructure | | No microstructure | |
| 0.2 | No microstructure | | No microstructure | | 3.4 ± 1.2 | 2.2 ± 0.7 |
| 2 | No microstructure | | 2.8 ± 0.8 | 2.0 ± 0.7 | 3.3 ± 1.2 | 2.3 ± 0.7 |
| 0 | 1.9 ± 0.5 | 1.4 ± 0.4 | 2.0 ± 0.5 | 1.5 ± 0.5 | 1.8 ± 0.5 | 1.2 ± 0.3 |

TABLE 3

Pore size distributions of collagen scaffolds with different photosensitizer dosages.

| [RB]/µM | Long axis | Short axis |
|---|---|---|
| | Pore size (micron) | |
| 0.1572 | — | — |
| 0.786 | 2.5 + 0.9 | 1.7 + 0.7 |
| 3.93 | 2.4 + 0.8 | 1.9 + 0.7 |
| 19.65 | 2.7 + 0.9 | 1.9 + 0.6 |
| 98.25 | 2.2 + 0.8 | 1.5 + 0.6 |

TABLE 4

Fiber size, volume fraction and mesh size of the fibrous meshwork in collagen microsphere of different treatment groups. (n = 3)

| | | Fiber sizes (nm) | Volume fractions | Mesh sizes (nm) |
|---|---|---|---|---|
| Without PC | Without Tween 20 | 49.45 ± 9.80 | 0.0079 ± 0.0006 | 414.11 ± 18.27 |
| | With Tween 20 | 44.31 ± 7.77 | 0.0086 ± 0.0007 | 353.39 ± 15.72 |
| With PC | Without Tween 20 | 51.70 ± 8.76 | 0.0094 ± 0.0016 | 395.83 ± 37.88 |
| | With Tween 20 | 42.28 ± 7.77 | 0.0088 ± 0.0004 | 332.17 ± 8.89 |

Example 6

BSA Release Pattern 25 mg of BSA was incorporated into 1 mg/ml of collagen microspheres as described in Example 1. Collagen microspheres were resuspended in 5 ml of 1×PBS in an Eppendoff tube and incubated in 37° C. water-bath with regular agitation at 200 rpm. 2 ml of the supernatant was removed with replacement at 0.5, 1, 2, 4, 8, 24 hours, 2, 4, 7, 14, and 35 days. The supernatant was diluted to the appropriate range for detection of the concentration of BSA using Bio-Rad protein assay kit.

Figure 4:
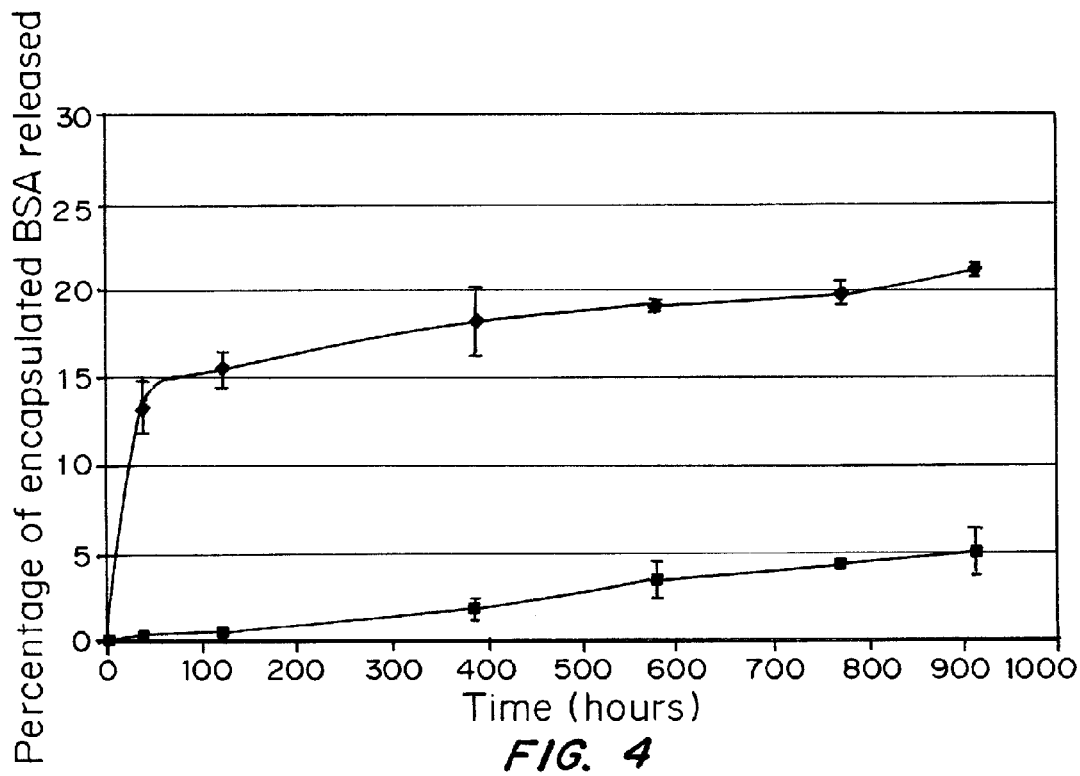
FIG. 4 is a line graph showing controlled release and reduced burst effect of BSA (percentage of encapsulated BSA) from microspheres with (-■-) or without (-♦-) 0.01% photocrosslinker ("PC") Rose Bengal ("RB"). The rate of release of BSA from the particles is graphed as encapsulated BSA released (percent) as a function of time (hours).
Figure 5:
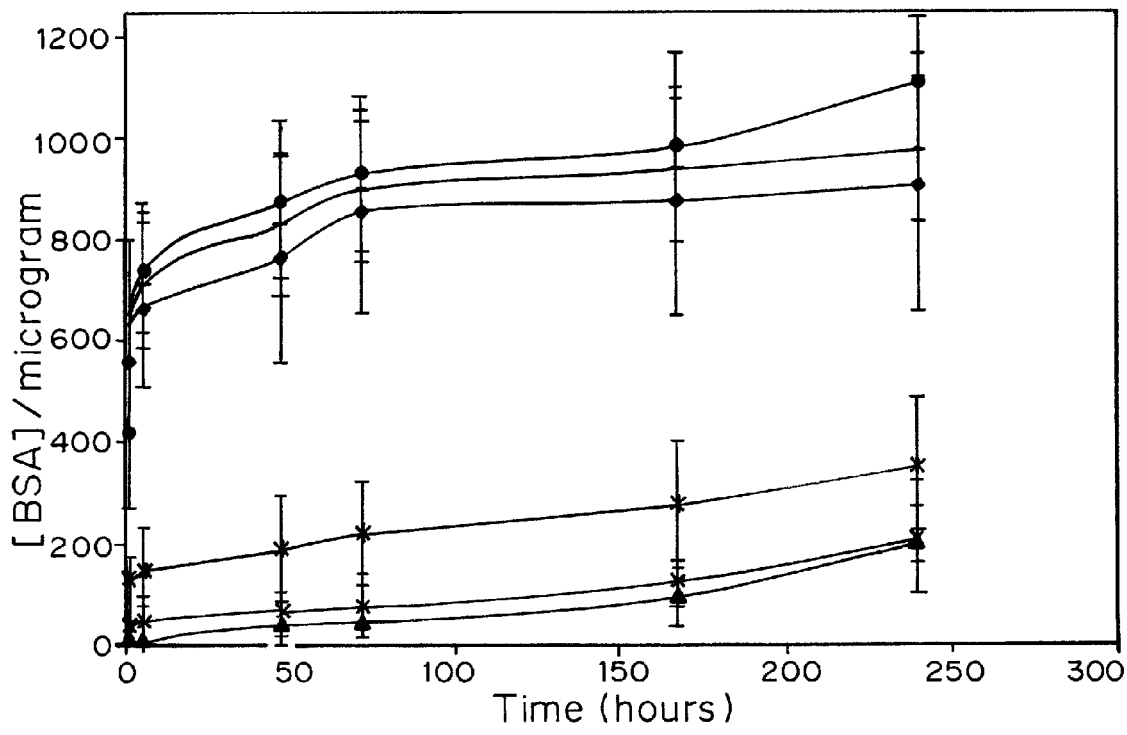
FIG. 5 is a line graph of the dose dependence of RB on release patterns of BSA. Tested concentrations of RB are 0 (-♦-), 0.01 (-▲-), 0.001 (-x-), 0.0001 (-*-), 0.00001 (-■-), and 0.000001 (-+-) percent. Release of BSA from the microparticles is graphed as concentration of BSA/microgram over time (hours).
Figure 6:
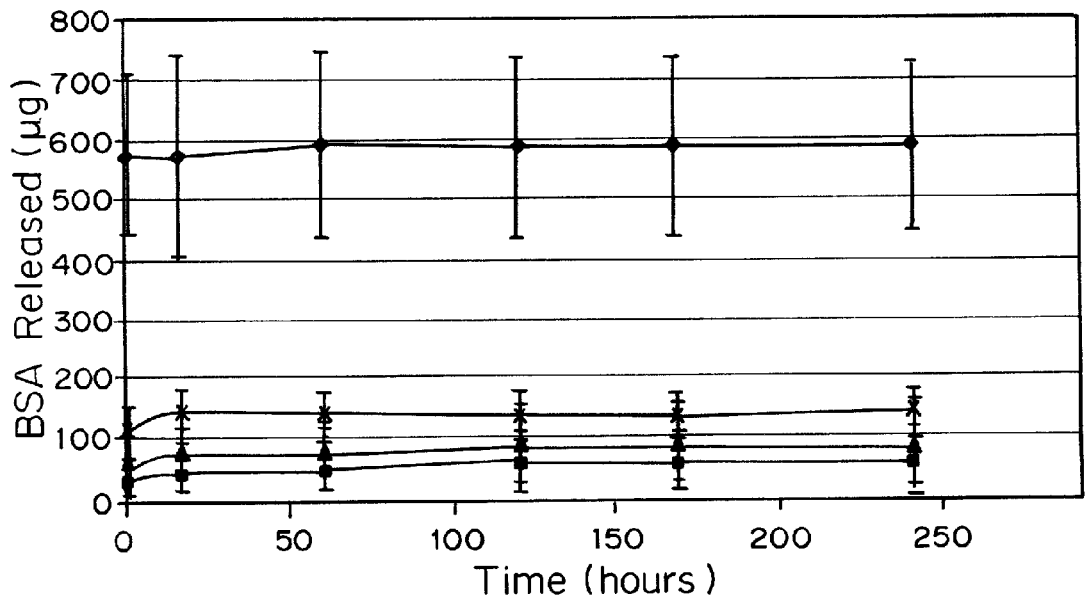
FIG. 6 is a line graph showing controlled release and reduced burst effect of microspheres with and without PC. Tested concentrations of RB are 0 (-♦-), 0.01 (-■-), 0.001 (-▲-), and 0.0001 (-x-) percent. BSA release from the microparticles is graphed as amount of BSA released (micrograms) as a function of time (hours).

FIGS. 4, 5 and 6 show that the photochemically crosslinked collagen microspheres have significantly reduced initial burst with an almost first order release kinetics of BSA. For the uncrosslinked microspheres, the initial burst effect resulted in a loss of almost 40% of the total amount loaded that significantly reduced the efficacy as drug delivery device in particular precious protein drugs. The release profile lasted for more than 35 days and the release is still linear in photochemically crosslinked microspheres.

Example 7

Retention of NGF Bioactivity after Photochemical Crosslinking and Surfactant Treatment 2.5 µg NGF in 5 mg BSA was incorporated into collagen microspheres as described in Example 1. Photochemical crosslinking was conducted as described in Example 2. Another group uses 1% Tween 20 as surfactant. The microspheres were suspended in 1 ml medium and incubated in 37° C. water bath for 1-4 days.

Figure 7:
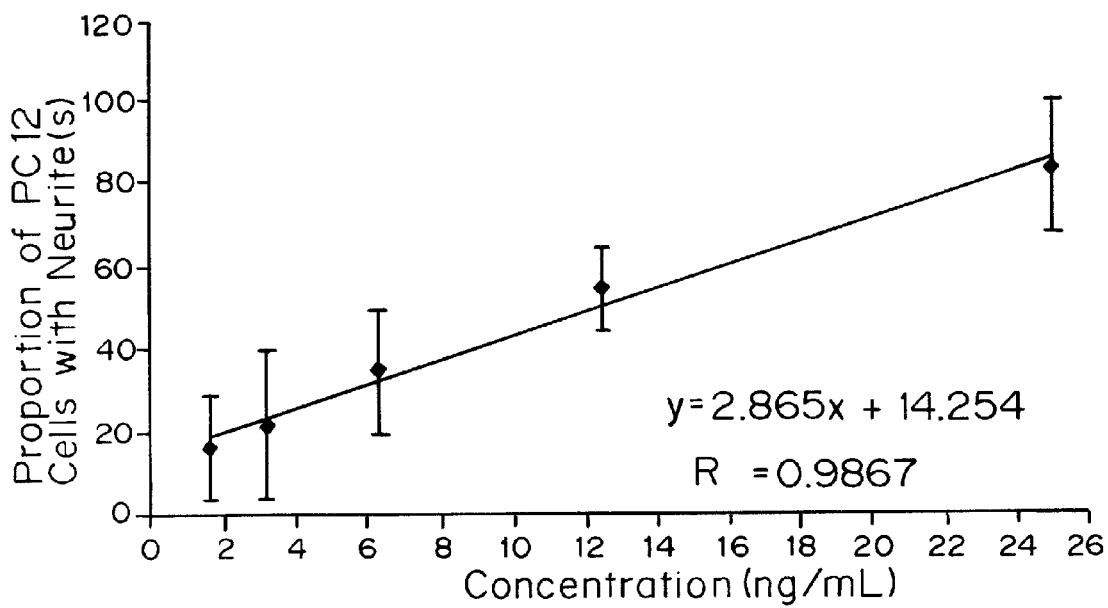
FIG. 7 is a line graph showing a standard curve of nerve growth factor (NGF) bioactivity as a function of concentration of NGF (ng/ml). NGF bioactivity was measured as the proportion of PC12 cells with neurite outgrowth longer than one body length using 1.5626, 3.125, 6.25, 12.5 and 25 ng/ml of NGF. Over 100 cells were counted in each group.

At the end of incubation, the supernatant was removed and used to incubate PC12 cells. PC12 cells were maintained in growth on 24-well plate in 81.5% F12K medium, supplemented with 15% Horse serum, 2.5% Fetal bovine serum and 1% PBS. The cells were cultured at 37° C. in a water-saturated 5% $CO_2$, 95% air atmosphere and plated at a density of approximately 3,000 cells (in 800 μl) per well. After 1-3 days, the cells were fixed for visualization under the phase microscope. Cells with neurite outgrowth longer than one body length of the cell were counted and the percentage of PC12 cells with neurite outgrowth was recorded. The amount of PC12 cells with neurite growth was calibrated against a standard curve using known concentrations of NGF. The standard curve is shown in FIG. 7. Part of the NGF released from the microspheres was incubated with PC12 cells while part of the sample was used for measurement of NGF concentration using ELISA. This allowed for a determination of the amount of released NGF that retained bioactivity.

The results demonstrated that NGF retained its bioactivity by stimulating PC12 differentiation and neurite growth as compared to the controls. Table 5 shows that the NGF released from microspheres treated with photochemical crosslinking or the surfactant retained almost all of their expected bioactivity, similar to those in the control.

TABLE 5

Retention of bioactivity of encapsulated NGF.

|  | Quantity of NGF measured by ELISA (ng) (mean ± SD) | Bioactivity of NGF measured by PC12 assay (ng) (mean ± SD) |
|---|---|---|
| Control | 28.67 ± 4.26 | 25.48 ± 11.63 |
| Tween 20 | 6.31 ± 0.73 | 5.42 ± 7.91 |
| PC | 3.14 ± 0.55 | 3.42 ± 4.9 |

Example 8

Retention of Bioactivity of NGF Immobilized Inside the Collagen Microspheres

In a separate experiment, NGF incorporated in the collagen microspheres was incubated at 37° C. for 1, 2, 3 and 4 days. At the end of each time point, the supernatant was discarded and the microspheres were digested with bacterial collagenase at 200 U/ml for 5 hours. The digestion mixture was then diluted into the appropriate range. Part of the sample was used to incubate with PC12 cells while part of the sample was used for concentration measurement using ELISA kit.

The results showed that NGF retained in the collagen microspheres is still bioactive even after 4 days as it induced neurite growth in PC12 cells.

Example 9

Measurement of Encapsulation Efficiency

Collagen microspheres were formed as described in Example 1, The aqueous phase separated from the microspheres and the oil phase was pooled with the rinses of the microspheres. The pooled solution was mixed well by vortexing and an aliquot of the washings was subjected to measurement of the incorporated BSA or myoglobin. The encapsulation efficiency was then calculated as follows:

[(total amount loaded−amount in the washings)/total amount loaded]×100%.

Figure 8:
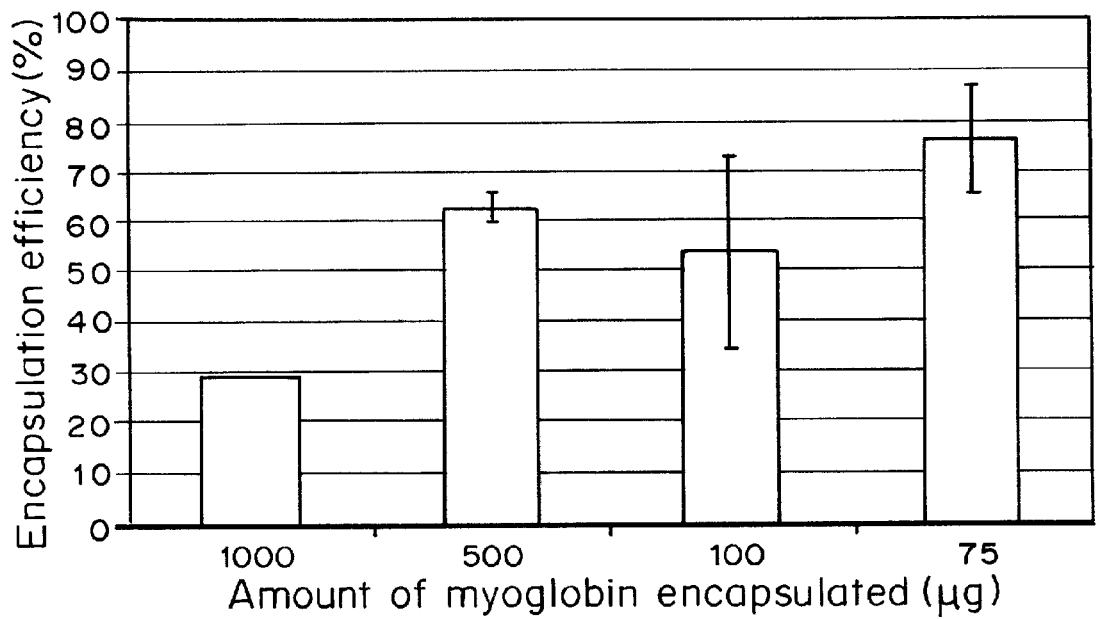
FIG. 8 is a bar graph showing control of encapsulation efficiency (percent) as a function of the amount of protein loaded, for 1000, 500, 100, and 75 micrograms.
Figure 9:
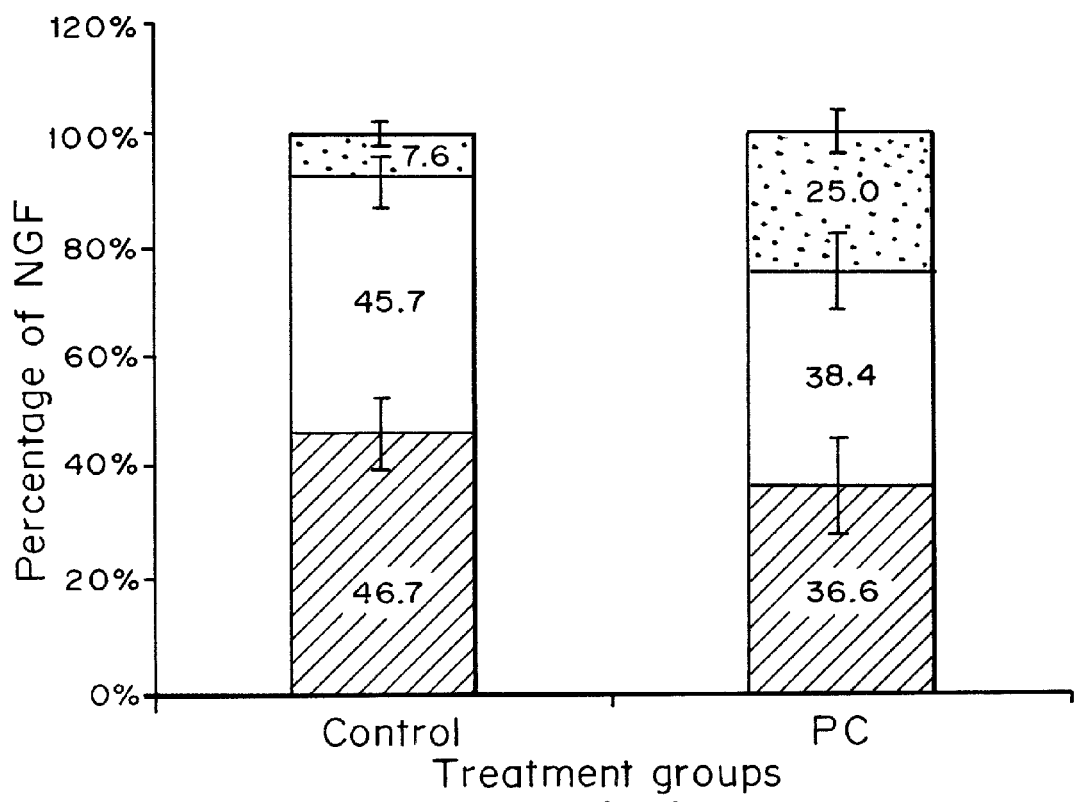
FIG. 9 is a bar graph showing the percentage distribution of NGF in collagen microspheres with and without photochemical crosslinking. (n=5). Stippled sections indicate the percentage of NGF that was retained by the microspheres. Open sections indicate the percentage of NGF that was released by the microspheres. Hatched sections indicate the percentage of NGF that was rinsed from the microspheres.

The total amounts of protein loaded and the concentration of the collagen used in microsphere formation were varied to study their effects on the encapsulation efficiency. FIG. 8 shows that the encapsulation efficiency decreases as the amount of protein being loaded increased. FIG. 9 shows that the amount of NGF retained in the photochemically crosslinked microspheres was higher than that in the uncrosslinked microspheres.

Example 10

Effects of Surfactant

Collagen microspheres were prepared as described in Example 1 except that a non-ionic surfactant TWEEN® 20 was additionally used. After incorporating the bioactive molecule, different concentrations of TWEEN® 20 (1, 5 and 10%) were mixed with the aqueous phase before addition of the oil phase. The emulsion was formed as described in Example 1 and the microspheres were separated from the liquid phase by centrifugation. The microspheres formed in the presence of surfactant were analyzed for morphology and release pattern.

The results show that an increase in surfactant concentration results in a more stabilized emulsion as shown by less phase inversion and more homogenous populations of the microspheres. Moreover, the size distribution of the microspheres has been shown shifted towards a smaller median value as the surfactant concentration increased.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method for preparing natural extracellular matrix-based microspheres, comprising
    providing an aqueous solution of one or more natural extracellular matrix components;
    initiating the sol-gel transition of the matrix components by initiating polymerization of the matrix components by raising the pH, the ionic strength or the temperature of the matrix components to form an aqueous gelling mixture;
    decelerating the sol-gel transition process by lowering the temperature, the pH or the ionic strength of the matrix components;
    incorporating therapeutic, prophylactic or diagnostic molecules into the aqueous gelling mixture;
    mixing the aqueous gelling mixture with an oil phase with agitation to form a water-in-oil emulsion;
    solidifying the microdroplets in the emulsion to form solid microspheres by increasing the pH, the ionic concentration or the temperature of the emulsion; and
    separating the solid microspheres from the oil phase and the aqueous phase.

2. The method of claim 1 further comprising photochemically crosslinking the microspheres to reduce the initial burst effect or control the release of the molecules from the microspheres.

3. The method of claim 2 comprising
equilibrating the microspheres with photosensitizing reagent; and
irradiating the microspheres with a light source for a period of time effective to crosslink some or all of the extracellular matrix components.

4. The method of claim 3 wherein the light source is a UV or visible light source operated at an irradiance variation of from 0.0001 W/cm$^2$ to 10 W/cm$^2$, and
wherein the irradiation energy ranges from 0.0001 J to 10000 J, for a period of irradiation ranging from 3 seconds to 100 hours.

5. The method of claim 4 wherein the light source is a UV or visible light source operated at an irradiance variation of about 0.2 W/cm$^2$, and
wherein the irradiation energy is about 25 J, for a period of irradiation of about 60 seconds.

6. The method of claim 2 wherein the photochemically crosslinked microspheres release the incorporated molecules with reduced initial burst effect as compared to non-photochemically crosslinked microspheres.

7. The method of claim 2 wherein the photochemically crosslinked microspheres release the incorporated bioactive molecules with a reduced rate as compared to non-photochemically crosslinked microspheres.

8. The method of claim 2 wherein the photochemically crosslinked microspheres release the incorporated molecules with first order release kinetics.

9. The method of claim 2 wherein the photochemically crosslinked microspheres retain more bioactive molecules in the matrix as compared to non-photochemically crosslinked microspheres.

10. The method of claim 2 wherein the incorporated bioactive molecules retain their bioactivities in photochemically crosslinked microspheres.

11. The method of claim 1 further comprising dehydrating the microspheres.

12. The method of claim 11 wherein the microspheres are dehydrated by immersion in an alcohol or glycerol.

13. The method of claim 1 wherein the natural extracellular matrix component is selected from the group consisting of collagen, gelatin, proteoglycan, hyaluronic acid, and elastin.

14. The method of claim 13 wherein the extracellular matrix component is collagen type I, II, III or mixtures thereof.

15. The method of claim 1 wherein the solution of extracellular matrix components contains monomers or the soluble states of the extracellular matrix components.

16. The method of claim 1 wherein the sol-gel transition is initiated by polymerization, precipitation or aggregation.

17. The method of claim 16 wherein the sol-gel transition is initiated by increasing the pH to between 4 and 14.

18. The method of claim 1 wherein the sol-gel transition of acid-soluble collagen is initiated by raising the temperature to 37° C.

19. The method of claim 1 wherein the sol-gel transition of the matrix components is initiated by increasing the ionic strength.

20. The method of claim 1 wherein the sol-gel transition of the matrix components is decelerated by lowering the pH or the temperature of the matrix components mixture.

21. The method of claim 1 wherein the aqueous gelling mixture is mixed with the oil phase to form an emulsion without fragmentizing the gelling mixture and disturbing the sol-gel transition process.

22. The method of claim 1 wherein the microspheres have size distributions ranging from 5 to 2000 microns.

23. The method of claim 1 wherein the microspheres are formed into structures for use in tissue engineering.

* * * * *

UNITED STATES PATENT AND TRADEMARK OFFICE
CERTIFICATE OF CORRECTION

| | | |
|---|---|---|
| PATENT NO. | : 7,931,918 B2 | Page 1 of 1 |
| APPLICATION NO. | : 12/166670 | |
| DATED | : April 26, 2011 | |
| INVENTOR(S) | : Barbara Pui Chan, Cheuk Ming Chan and Kwok Fai So | |

It is certified that error appears in the above-identified patent and that said Letters Patent is hereby corrected as shown below:

Cover Page, (75) Inventors, replace "Ming Cheuk" with --Cheuk Ming--.

Signed and Sealed this
Twentieth Day of September, 2011

David J. Kappos
*Director of the United States Patent and Trademark Office*